United States Patent [19]
Nicolau et al.

[11] Patent Number: 5,677,176
[45] Date of Patent: Oct. 14, 1997

[54] ANIMAL DERIVED CELL WITH ANTIGENIC PROTEIN INTRODUCED THEREIN

[75] Inventors: Yves-Claude Nicolau; Garret M. Ihler, both of College Station, Tex.

[73] Assignee: Hapgood, C.V., Oldwick, N.J.

[21] Appl. No.: 404,372

[22] Filed: Mar. 15, 1995

Related U.S. Application Data

[63] Continuation of Ser. No. 46,384, Apr. 9, 1993, abandoned, which is a continuation of Ser. No. 771,874, Oct. 2, 1991, abandoned, which is a continuation of Ser. No. 197,445, May 27, 1988, abandoned, which is a continuation-in-part of Ser. No. 68,288, Jun. 30, 1987, abandoned.

[51] Int. Cl.$^6$ .............................. C12N 5/06; C07K 14/00
[52] U.S. Cl. .............................. 435/325; 530/350
[58] Field of Search .................. 435/173.4, 71.3, 435/240.1, 325; 530/350; 536/23.5

[56] References Cited

U.S. PATENT DOCUMENTS 5,236,835  8/1993  Mouneimne et al. ............... 435/173.6

OTHER PUBLICATIONS

Doxsey et al. An efficient method for introducing macromolecules into living cells J. Cell Biol. vol. 101 19–27 1985.

Maddon et al. The isolation and nucleotide sequence of a cDNA encoding the T cell surface protein T4: A new member of the immunoglobulin gene family Cell vol. 42 93–104 1985.

Gad et al. Fusion of cells and proteoliposomes: Incorporation of beef heart cytochrome oxidase into rabbit erythrocytes FEBS Lett. vol. 102 230–234 1979.

Mayhew et al. Therapeutic applications of liposomes Chapter 7 in Liposomes M.J. Ostro Ed. Marcel Dekker, New York and Basel. 1983.

Dimitriadis et al. Liposome-mediated ricin toxicity in ricin-resistant cells FEBS Lett. vol. 98 33–36 1979.

Yarchoan et al. Administration of 3'-azido-3'-deoxythymidine, an inhibitor of HTLV–III/LAV replication, to patients with AIDS or AIDS-related complex Lancet 575–580 Mar. 15, 1986.

*Primary Examiner*—James Ketter
*Assistant Examiner*—John S. Brusca
*Attorney, Agent, or Firm*—Baker & Botts, L.L.P.

[57] ABSTRACT

This invention comprises animal derived cells, especially erythrocytes, which have been artificially modified (and referred to as engineered erythrocytes or RBCs) so as to incorporate in their plasma membranes an antigen, CD4 protein derived from lymphocytes) which will cause them to selectively seek out and fuse with other cells that are infected with a virus, especially the AIDS virus. These modified cells can be further altered so as to contain in their cytoplasm a cytotoxic agent which, after the cell has fused with a target cell, will result in the pooling of their respective cytoplasms and the death of both cells. Such modified cells can be used as a basis for an in vitro diagnostic assay involving cells derived from the blood of patients suspected of having AIDS.

4 Claims, No Drawings

ANIMAL DERIVED CELL WITH ANTIGENIC PROTEIN INTRODUCED THEREIN

This application is a continuation of U.S. application Ser. No. 08/046,384, filed Apr. 9, 1993, now abandoned, which is a continuation of U.S. application Ser. No. 07/771,874, filed Oct. 2, 1991, now abandoned, which is a continuation of U.S. application Ser. No. 07/197,445, filed May 27, 1988, now abandoned, which is a continuation-in-part of U.S. application Ser. No. 07/068,288, filed Jun. 30, 1987, now abandoned.

BACKGROUND OF THE INVENTION

1. Field of the Invention

The present invention relates to an animal derived cell into whose membrane is introduced an antigenic protein which predisposes the cell to bind and fuse with other cells. More particularly, the present invention concerns modified cells and liposomes, wherein their outer membranes have incorporated therein specific protein substances which will cause the modified cells or liposomes to bind selectively, in vivo and in vitro, to various target cells, especially those infected with a virus, e.g., the human immunodeficiency virus (hereafter HIV).

2. Background Information

It is known that Acquired Immune Deficiency Syndrome (AIDS) is a virulent disease characterized by a well defined chronological sequence of symptoms and a high rate of mortality (Curran, J. W. et al, The Epidemiology of AIDS, Science, 229, 1352–1357 (1985)). AIDS was first described in 1981 and since that time has reached epidemic proportions with some 400,000 cases in the United States alone and a 3 year mortality rate of over 90%. It is now estimated that approximately 1 million people in this country have been infected with the human immunodeficiency virus (HIV). HIV is classified as a retrovirus containing core proteins, genomic RNA, and the enzyme reverse transcriptase. Antibodies to several antigens of HIV are present in the serum of infected persons.

The hallmark of the immunodeficiency in AIDS is depletion of the T4 helper/inducer lymphocytes (Gottlieb et al, N. Engl. J. Med. 305, 1425–1431 (1981)). This defect is primarily the result of selective infection by HIV of this population of lymphocytes. The T4 molecule (denoted CD4 antigen) present on the surface of helper lymphocytes has been implicated as the receptor for the HIV virus (Dalgleish et al, Nature, 312, 763–767 (1984)) which enters the cell after specific binding to the surface of the T4 lymphocyte. The mechanism of viral entry has not been completely defined but it may be similar to either receptor-mediated endocytosis or direct fusion of the HIV envelope with the cell membrane (Stein et al, Cell 49, 659–668 (1987)).

A fusogenic protein, called gp120 (a glycoprotein of molecular weight 120,000 daltons) (McDougall et al, Science, 231, 382–385 (1986)) has been identified on the HIV surface and this protein may serve to mediate fusion between the virus and the lymphocyte. Once inside the cell, the viral RNA is transcribed into DNA by reverse transcriptase. Subsequently, the DNA is integrated into the host genome. However, most of the HIV DNA remains unintegrated and in the cytoplasm. It is now known that HIV replication is restricted at this stage until the infected cell is "activated" (McDougal et al, J Immunology, 135, 3151–3162 (1985)). It is believed that the potential activators of replication, following HIV infection, include viruses such as hepatitis B, human cytomegalovirus, and herpes simplex virus. Upon activation, the HIV is replicated and then assembled on the cell surface. Mature virions are then formed by budding from the surface membrane of the T4 lymphocyte. Subsequent to initiation of HIV replication, the T4 lymphocyte may be killed.

While the cytopathic effect of HIV virus for T4 lymphocytes is presently unknown, it has been observed that when HIV infection occurs, the viral gp120 antigen is expressed on the surface of the infected T4 lymphocyte. Because of the affinity of this protein for the normally present CD4 antigen, other T4 lymphocytes (uninfected and possessing the CD4 antigen) can fuse with the infected lymphocyte. The resulting binding and fusing of the cells appears to kill both, or all, of the cells involved in the fusion (Zagury et al, Science, 231, 850–853 (1986)). For example, T4 lymphocytes from cell lines which lack the CD4 antigen on their surfaces as well as T4 cells in which the antigen has been masked by reaction of the cells with anti-CD4 antibodies do not demonstrate fusion with HIV-infected T4 cells under the usual conditions (McDougall, supra).

This fusion process can involve a few HIV-infected and a large number of noninfected T4 cells and could lead to the formation of large syncytia which could then either be removed from the circulation by the cells of the reticuloendothelial system or else lyse (e.g., in organs like the brain) (Shaw et al, Science, 227, 177–181 (1985); Gartner et al, Science, 233, 215–219 (1986)).

The T4 lymphocyte plays a central role in the immune response. It is intimately involved with macrophages, cytotoxic T cells, NK (natural killer) cells and B lymphocytes. Therefore, even a selective depletion of the T4 lymphocyte population can result in a multitude of immunologic defects leading to the life-threatening opportunistic infection characteristic of AIDS (Bowen et al., Ann Intern Med, 103, 704–709 (1985)). In addition, certain populations of monocytes and macrophages also express the CD4 antigen and studies have shown that these cells can also become infected with HIV (Ho et al, J Clin Invest, 77, 1712–1715 (1986)). HIV infection of monocytes can result in a defect in chemotaxis which has been reported in AIDS. The infected macrophages may carry the HIV virus into the central nervous system allowing for the development of the subacute encephalitis that occurs in this disease (Gabuzda et al, Ann Neurology, 20, 289–295 (1986)). HIV infected monocytes may produce a variety of factors, including tumor necrosis factor, that could explain the chronic fever of AIDS and also the associated condition of cachexia (general malnutrition).

Furthermore, B lymphocyte abnormalities, consisting of polyclonal activation with high levels of immunoglobulin coupled with poor antibody response to new antigens are common with AIDS and may be a direct consequence of the HIV infection. Patients in the more advanced stages of AIDS are usually anergic (i.e., exhibit diminished immunological response to common antigens).

AIDS has proven extremely difficult to treat, let alone cure. Heretofore, several different approaches have been tried. Among the potential treatments currently being investigated are the following:

a. Inhibitors of reverse transcriptase. This type of treatment can be highly selective because the target enzyme is not found in human cells. The prototype drug in this class is azido-3'-deoxythymidine (AZT). This drug has passed through phase I, II, and III studies and is presently approved for treating patients with AIDS and who have had previous pneumocystis infection. Studies have shown that patients treated with this drug exhibit increased levels of helper T lymphocytes and about a third demonstrate positive skin test (where the latter were previously anergic). In addition, there is an improvement over the neurological deficiencies characteristic of the disease (see Yarchoan et al, *Lancet*, pp 575–580 (1986)). However, despite the aforestated improvements in clinical and immunological parameters, the virus is found to persist in lymphocytes.

b. General antiviral agents. Currently under investigation are such compounds as ribavirin, Foscarnet (HPA-23), and suramin. No data is presently available on the effectiveness of these agents.

c. Immunomodulators. This type of treatment involves attempts to enhance or reconstitute the defective immune system in patients with AIDS. Such trials have been taking place for several years. Among the immunomodulators being examined are Alpha Interferon, a leukocyte-derived glycoprotein possessing antiviral immunoregulatory and anti-proliferative effects. This agent has exhibited only minimal effectiveness in human patients while showing unacceptable toxicity levels (Celmann et al, *Am J Med*, 78, 737–741 (1985)). A similar agent tested in AIDS patients is Interleukin-2. The latter has been shown to elevate the total number of T-lymphocytes, and to decrease, but not eliminate, the isolation of HIV from lymphocytes. It has also been implicated in minor degrees of regression of Kaposi's sarcoma, the latter a malignant tumor associated with the more advanced stages of AIDS (Broder et al, *Lancet*, pp 627–630 (1985)).

d. Transplantation. Bone marrow transplantation has been attempted in several AIDS patients, the purpose being to reconstitute their immunologic reactivity. Such therapy has resulted only in transient, rather than long lasting, improvement in the condition.

Methods of efficiently fusing liposomes with either cells or nuclear envelopes have been described (see Arvinte et al, *Biochemistry*, 26, 765–772 (1986)). In most instances such fusions have been achieved using inducing agents, called fusogens, which may be proteins, peptides, polyethylene glycol, viral envelope proteins, etc. In some cases the fusion inducing agent involves altered conditions of the medium. Thus, lowered pH has been used advantageously to induce fusion of liposomes with nuclear envelopes (Arvinte et al, *Biochemistry*, supra).

Procedures have been previously developed for the targeted delivery of different molecules to specific cells in vivo (Wicolau et al, *Biochim. Biophys. Acta*, 805, 354–367 (1984)). Such targeting was realized by using liposomes which contained specifically selected glycolipids in their bilayers. Such glycolipids were selected based upon the presence on them of a terminal carbohydrate portion which was recognized by one or more lectins (substances derived from plant cells which bind specifically to certain types of carbohydrate structures) on the target cell's plasma membrane (see Wicolau et al, *Proc Natl Acad Sci*, 80, 7128–7132 (1983)). For such a procedure will work, the target cell must contain a receptor in its membrane which is specific for, and will bind to, a molecule present in the membrane of another cell. It is then necessary to induce the cells to fuse which can be accomplished experimentally using fusogenic agents, or, in nature, by certain fusing agents such as proteins derived from viral infection (Gallo et al., *Science*, 224, 500–503 (1983)).

SUMMARY OF THE INVENTION

It is an object of this invention to take advantage of the selective fusion of HIV-infected cells with CD4-bearing cells by producing CD4-bearing cells, advantageously erythrocytes, and alternatively, liposomes, into which have been incorporated various cellular toxins and lytic agents, advantageously the protein ricin. Such a procedure results in the selective killing of HIV-infected cells. Such object is realized by the construction of a family of engineered red blood cells or liposomes carrying the CD4 antigen in the plasma membrane or lipid bilayer (as the case may be) and containing a cytotoxic agent such as ricin, gelonin, and/or equivalents thereof.

It is a further object of this invention to present procedures for the introduction of antigens into the plasma membranes of cells.

It is also an object of this invention to present procedures for the incorporation of toxic and cytolytic agents into liposomes and cells of choice.

It is another object of this invention to alleviate viral disease conditions by the introduction into a patient so afflicted an optimal quantity of such engineered cells or liposomes and allowing these cells or liposomes to bind to, fuse with an destroy viral infected cells in vivo, before the virus can either replicate in the infected target cell or facilitate that cell's binding to other healthy cells so as to spread the virus or retard the body's defenses against it.

It is also an object of this invention to present a procedure for the administration of heterologous red blood cells (and/or liposomes) altered by insertion of the CD4 protein into their membranes with resultant selective binding of these cells (and/or liposomes) to cells infected with HIV and concomitant fusion and elimination from the circulation of the HIV infected cells.

These and other objects, aims and advantages are realized in accordance with the present invention.

The present invention concerns an animal, e.g., human, derived cell into whose membrane has been introduced, e.g., artificially incorporated, an antigenic protein which predisposes the cell to bind to and fuse with other cells.

The present invention also relates to a treatment of a virus induced disease which comprises administering, e.g., injecting, thereof a therapeutically effective amount of the aforementioned animal derived cells in conjunction with one or more cytotoxic agents, suspended in a pharmacologically acceptable diluent.

The present invention is also directed to a composition comprising a therapeutically effective amount of the aforesaid animal derived cells, in conjunction with one or more cytotoxic agents, suspended in a pharmacologically acceptable diluent.

DETAILED DESCRIPTION OF THE INVENTION a. Nature of the Invention

The present invention embodies a type of engineered red blood cell which has incorporated into its plasma membrane the human CD4 antigen and contains within the cell one or more cytotoxic agents capable of destroying any cell which fuses with the engineered cell. In place of these engineered red blood cells, liposomes can be produced and used in a similar manner. The invention also relates to a procedure for producing these cells from normal red blood cells. The invention further embodies a method for using these engineered red blood cells (or liposomes) to treat diseases caused by viral infection, especially Acquired Immune Deficiency Syndrome (AIDS). It should be kept in mind, of course, that whenever engineered red blood cells are referred to, the modified liposomes described herein can also be used.

The major feature of the proposed treatment is as follows. Red blood cells carrying on their membrane the CD4 receptors are capable of binding to circulating HIV-infected cells expressing the viral gp120 surface glycoprotein. Such aggregates are then removed from the circulation by splenic macrophages and the Kupffer cells of the liver.

In order to prevent the possible infection of these phagocytic cells upon uptake of the cellular aggregates, certain anti-HIV drugs such as AZT- or DDC-triphosphate (where AZT is azido-3'-deoxythymidine and DDC is dideoxycytidine) are encapsulated in CD4-bearing erythrocytes prior to injection. Although phagocytosis without drugs effectively leads to the destruction of the HIV-infected cells, additional protection results by incorporating such anti-HIV drugs in the red cells.

Because the HIV-infected cells tend to selectively bind and eventually fuse with noninfected cells having the CD4 antigen we postulated and proved that any cells, even erythrocytes, possessing this antigen on their plasma membranes would selectively bind and possibly fuse with HIV-infected T-cells and/or with the HIV virus itself. When an HIV-infected cell fuses with another cell containing a cytolytic agent the infected cell is destroyed.

To be clinically effective as an agent in the destruction of virus infected cells the engineered cells must have the following properties: 1. they must be long lasting, i.e., have a lifespan at least approaching the normal lifespan of the cell, in this case erythrocytes, in vivo; 2. they must be of low toxicity so that the cytotoxic agent contained in them will not act indiscriminately on the tissues of the body; 3. they must not themselves be adversely affected by the toxin placed within them (otherwise they would be poisoned before they could seek out and selectively fuse with the target cell); 4. they must also be selective in fusing only with the target (i.e. infected) cell and neither bind to nor fuse with other healthy cells; 5. they must be non-immunogenic so that they will not cause an adverse antigenic reaction in the recipient and thus further tax the patient's already stressed immune system. The modified erythrocytes (and liposomes) comprising the present invention have been discovered to be good candidates for such a role. This is because they lack any of the vital reproductive apparatus of other cells and, during their life-spans, are essentially nothing more than bags of hemoglobin which serve to carry oxygen in the blood stream. Thus, they are not themselves adversely effected by the presence within them of various cytotoxic agents. Since erythrocytes are among the most numerous cells in the bloodstream the replacement of a small portion of them by antigenically-modified toxin-laden cells is of little consequence to the organism. Additionally, because the toxin is sequestered within the modified erythrocytes it is not free to interact randomly with the tissues of the organism as would be the case with a more injected therapeutic agent.

b. Liposomes

Consist of spheres of lipid bilayers (two-molecules thick) that enclose an aqueous medium.

Liposomes can generally be formed by sonicating a lipid in an aqueous medium, by resuspension of dried lipid layers in a buffer or by dialysis of lipids dissolved in an organic solvent against a buffer of choice.

Phospholipids form closed, fluid-filled spheres when they are mixed with water in part because the molecules are amphipathic: they have a hydrophobic (water-insoluble) tail and a hydrophilic (water-soluble), or "polar," head. Two fatty acid chains, each containing from 10 to 24 carbon atoms, make up the hydrophobic tail of most naturally occurring phospholipid molecules. Phosphoric acid bound to any of several water-soluble molecules composes the hydrophilic head. When a high enough concentration of phospholipids is mixed with water, the hydrophobic tails spontaneously align together to exclude water, whereas the hydrophilic heads bind to water.

The result is a bilayer in which the fatty acid tails point into the membrane's interior and the polar head groups point outward. The polar groups at one surface of the membrane point toward the liposome's interior and those at the other surface point toward the external environment. It is this remarkable reactivity of phospholipids with water that enables workers to load medications into liposomes. As a liposome forms, any water soluble molecules that have been added to the water are incorporated into the aqueous spaces in the interior of the spheres, whereas any lipid soluble molecules added to the solvent during vesicle formation are incorporated into the lipid bilayer.

Liposomes employed for drug delivery typically range in diameter from 250 angstrom units to several microns (for comparison, the diameter of an erythrocyte is about 10 microns) and are usually suspended in a solution. They have two standard forms: "onion-skinned" multilamellar vesicles (MLV's), made up of several lipid bilayers separated by fluid, and unilamellar vesicles, consisting of a single bilayer surrounding an entirely fluid core. The unilamellar vesicles are typically characterized as being small (SUV's) or large (LUV's).

Under appropriate circumstances liposomes can adsorb to almost any cell type. Once they have adsorbed the spheres, liposomes may be endocytosed, or swallowed up, by some cells. Adsorbed liposomes can also exchange lipids with cell membranes and may at times be able to fuse with cells. When fusion takes place, the liposomal membrane is integrated into the cell membrane and the aqueous contents of the liposome merge with the fluid in the cell.

The ability of liposomes to adsorb, bind and eventually be taken up by many types of cells and then slowly release their contents makes them excellent candidates for time-release drug-delivery systems. How quickly a drug is released from a liposome depends on numerous factors, including the composition of the liposome, the type of drug encapsulated and the nature of the cell.

Endocytosis of liposomes occurs in a limited class of cells, viz., those able to ingest foreign particles. When phagocytic cells take up liposomes, the cells move the spheres into subcellular organelles known as lysosomes, where the liposomal membranes are believed to be degraded. From the lysosome, the liposomal lipid components probably migrate outward to become part of the cell's membranes and other liposomal components that resist lysosomal degradation (such as certain medications) may enter the cytoplasm.

Lipid exchange involves the transfer of individual lipid molecules from the liposome into the plasma membrane (and vice versa); the aqueous contents of the liposome do not enter the cell. For lipid exchange to take place the liposomal lipid must have a particular chemistry in relation to the target cell. Once a liposomal lipid joins the cell membrane it can either remain in the membrane for a long time or be redistributed to a variety of intracellular membranes. If a drug was somehow bound to such an exchangeable lipid, it could potentially enter the cell during lipid exchange.

c. Diseases

The present invention can be used to combat various viral, bacterial, allergen and parasitic diseases of man and animals.

Accordingly, the present invention can be used to combat the following viruses: HIV, hepatitis B virus, influenze hemagglutinin (A/memphis/102/72 sttain, A/Eng 1878/69 strain, A/NT/60/68/29c strain, and A/Qu/7/70 strain, Ao/PR8/34, A1/CAM/46, and A2/Singapore/1/57; Type B influenze viruses, e.g. B/Lee 40), fowl plague virus hemagglutinin, vaccinia, polio, rubella, cytomegalovirus, small pox, herpes simplex types 1 and 2, yellow fever, Infectious ectromelia virus, Cowpox virus, Infectious bovine rhinotracheitis virus, Equine rhino-pneumonitis (equine abortion) virus, Malignant catarrh virus of cattle, Feline rhinotracheitis virus, Canine Herpes virus, Epstein-Barr virus (associated with infectious mononucleosis and Burkitt lymphoma), Marek's disease virus, Sheep pulmonary adenomatosis (Jaagziekte) virus, Cytomegaloviruses, Adenovirus group, Human papilloma virus, Feline panleucopaenia virus, Mink enteritis virus, Infectious pancreatic necrosis virus of trout, Fowl sarcoma virus (various strains), Avian leukosis virus (visceral, erythroblastic and myeloblastic), Osteopetrosis virus, Newcastle disease virus, Parainfluenze viruses 1, 2, 3, and 4, Mumps virus, Turkey virus, CANADA/58, Canine distemper virus, Measles virus, Respiratory syncytial virus, e.g., B influenze viruses, e.g., B/Lec/40; Rabies virus; Eastern equine encephalitis virus; Venezuelan equine encephalitis virus; Western equine encephalitis virus; Yellow fever virus, Dengue type 1 virus (=type 6), Dengue type 2 virus (=type 5), Dengue type 3 virus, Dengue type 4 virus; Japanese encephalitis virus; Kyasanur forest virus; Louping ill virus; Murray Valley encephalitis virus; Omsk hemorrhagic fever virus (types I and II); St. Louis encephalitis virus; Human rhinoviruses; Foot-and-mouth disease virus; Poliovirus type 1; Enterovirus Polio 2; Enterovirus Polio 3; Avian infectious bronchitis virus; Transmissible gastro-enteritis virus of swine; Lymphocytic choriomeningitis virus; Lassa virus; Machupo virus; Pichinde virus; Tacaribe virus; Papillomavirus; Sindbis virus; and the like.

The present invention can also be used to combat bacteria such as those causing leprosy, tuberculosis, syphilis and gonorrhea.

The present invention can also be used to combat parasites, for example, organisms carrying malaria (Plasmodium falciparum, P. ovale, etc.), Schistosomiasis, Onchcerca volvulus and other filiarial parasites, Trypanosomes, Leishmania, Chargas disease, amoebiasis, hookworm, and the like.

Since the present invention permits targeting of the modified cells and liposomes to particular cells and tissues, it can also be effective in combating cancerous growths.

e. Production of Pure CD4

The destruction of normal T-cells by HIV involves the infectiono f the cell by the virus with subsequent production of specific glycoproteins coded for by the virus and insertion of these glycoproteins into the plasma membrane of the infected cell. This glycoprotein has an affinity for other cells which contain the CD4 antigen on their surfaces. The human leukocyte antigen, CD4 can be isolated from various sources including the buffy coat obtained following centrifugation of blood from a blood bank as well as from a T-cell lymphoma cell line (CEM-cells obtained from the American Type Culture Collection, Rockville, Md., USA). A CD4 antigen can be purified by the procedure of Maddon et al., Cell, 42, 93–104 (1985).

A general scheme for this procedure is shown hereinbelow as follows:

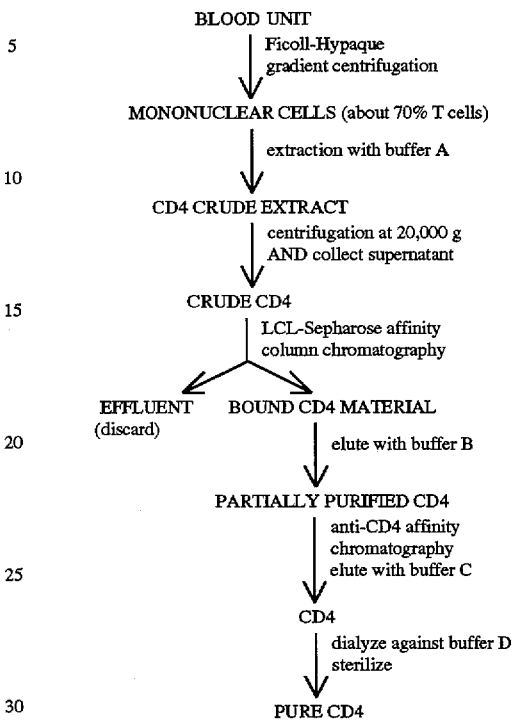

Purified CD4 is ready for use and is stable for 2–3 months at −20° C. In the above scheme, the buffer compositions could be as follows:

Buffer A=0.2M n-octyl-β-D-galactoside (OGS) 0.15M NaCl 0.2M PMSF 0.01M Tris, final pH=8.0.

Buffer B=Buffer A containing 0.1M beta-mannoside

Buffer C=1% (w/w) Sodium deoxycholate 1M Sodium Acetate, final pH=4.0.

Buffer D=0.1M Acetate, pH=4.7.

In Buffer A, above, PMSF (phenyl methyl fluorosulfonic acid) is a toxic substance used to inhibit proteolysis during the extraction and purification procedure. However, it is completely removed by the subsequent chromatography steps.

OGS (octyl-galactoside) is a detergent used in the extraction of CD4. Later in the purification process, it is replaced by DOC (deoxycholate), which is a naturally occurring bile salt and is not toxic.

DOC (sodium deoxycholate) will be present in purified CD4 at a concentration of 0.005% and in the blood of AIDS patients treated by the present invention at a concentration of about 0.000001% (which is completely safe).

Human CD4 protein can also be obtained as a recombinant CD4 molecule in a variety of cells (Walton et al, Cell, 1988, in press.

f. Cell Fusion to Form Engineered Red Blood Cells

A general procedure for formation of engineered erythrocytes according to the present invention is outlined hereinbelow as follows:

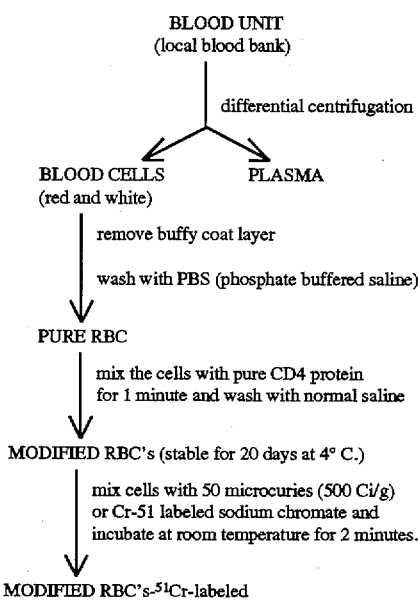

The modified-RBC's (red blood cells) produced in the above scheme (unlabeled) contain about 50,000 molecules of CD4 per cell and are stable at 20° C. for up to 20 days.

The chromium labeled modified RBC's were used for toxicity studies only, so that their production is optional and they should normally not be used in the actual practice of this invention for therapeutic purposes, although they could be. Such labelled cells would find use in in vitro diagnostic procedures using the present invention as the active reagent therein.

An alternative procedure for insertion of CD4 into erythrocyte membranes is to first insert the protein into liposome membranes and then fuse them with erythrocytes to yield a cell-liposome hybrid containing CD4 in the membrane. In addition, this procedure results in the delivery of a liposome-encapsulated molecule (advantageously, a cytotoxin or a therapeutic agent) to a cell, advantageously an erythrocyte, with subsequent fusion.

Techniques for the continuous lysis and resealing of erythrocytes have been developed, i.e., based on the already known concept of resealed red cells (Ihler et al, *PNAS,* 70, 2663–2666 (1973)), and cells loaded by endocytosis (Ihler et al, *J. App. Biochem.,* 4, 418–435 (1982)). These procedures permit the encapsulation of a wide variety of molecules into cells while keeping their life-spans unchanged (Nicolau et al., EP 83 401364-1 (1983) and Nicolau et al, *Ann. N.Y. Acad. Sci.,* 445, 304–315 (1985). The present invention involves a modified erythrocyte (or liposome) which can act as a "targeted bullet" for ultimate fusion with, and destruction of, virus infected cells in vivo.

It has already been shown that lysozyme will induce fusion of liposomes with erythrocyte ghosts at acidic pH (Arvinte et al., *Proc. Nat. Acad. Sci.,* Vol. 83, 962–966 (1986)). In that procedure the lysozyme was covalently bound to the outer surface of sonicated vesicles (liposomes) and served to induce fusion of these vesicles with human erythrocyte ghosts. A strong induction of fusion was found at the lysozyme pH optimum (which was not observed when lysozyme was merely added to the suspension). This procedure is useful because the lysozyme does not induce fusion of electrically neutral liposomes with each other and thus is well suited for fusing liposomes with cells.

The present invention involves procedures for inducing fusion without lysozyme being present in the medium at all. This greatly facilitates the formation of engineered erythrocytes for large scale clinical use.

g. Toxicity of Engineered Erythrocytes

The lifespan of engineered red blood cells (containing different entrapped substances, such as inositol hexaphosphate isothiocyanate-labeled ricin) has been shown to be very nearly the normal value (Nicolau et al, *Ann. N.Y. Acad. Sci.,* supra). In addition, the in vivo toxicity of these cells over a period of 30 days in piglets has been followed. Briefly, after injection of a small quantity of the engineered cells (about 0.1 to 1 ml of 30 to 40% drug-laden cells, i.e. the hematocrit of the cell suspension is 30 to 40%, injected intravenously) samples of the animal's blood, e.g., piglet's blood, are withdrawn at intervals of time over the course of thirty days. These are assayed for levels of ions (including K, Na, Cl, Ca, etc) as well as protein, urea and glucose levels.

Life span measurements of mouse RBC's encapsulating gelonin have shown no significant change as compared with the lifespan of normal mouse RBC's (both having a half life of about 11 days in mice).

During toxicity experiments, animals are sacrificed at various time intervals over a thirty day period and the state of the liver Kupffer cells and splenic macrophages is examined. Direct innoculation of free immunotoxin (where ricin was the toxin) has shown tissue damage in the reticuloendothelial system. The macrophages in the spleen and liver remove the toxin from circulation (Vitetta et al, *Science,* 219, 644–650 (1983)). However, there is no damage to kidney cells by the immunotoxins used according to the present invention, showing that the toxin-laden engineered cells are not toxic. For other engineered red cells the main target for the contained toxin would be the splenic macrophages. Since these cells can be replaced by stem cells, any resulting damage would not be irreversible. Further, experimental evidence has pointed to the impossibility of exhausting the reticuloendothelial system because of the replacement of macrophages from cells in the bone marrow (Van Furth and Cohn, *J. Exp. Med.,* 128, 415–424 (1968)).

h. Fusion With Target Cells

Since T4 cells, required for proper immune system functioning, possess the CD4 antigen they will selectively bind to the infected cells and ultimately be lysed. Lysis can be measured in vitro by incorporation, into cultured cells, of radioactive moieties, e.g., Cr-51. Release of the isotope into the medium above the cells (monitored using a well-type counter) is a measure of lysis. Such lysis correlates with the formation of syncytia (as generated by the fusion of CD4-containing cells with HIV-infected cells). Such fusion was monitored by the procedure of Example 5, infra, with results shown in the corresponding Table 1, given hereinbelow.

Erythrocytes into which has been inserted CD4 antigen can be examined by freeze-etching electron microscopy as well as by thin section electron microscopy. Briefly, erythrocytes with CD4-antigen are incubated with mouse monoclonal anti-CD4. After washing, these cells were incubated with 10 nm gold beads which are coated with goat anti-mouse IgG. In freeze-fracture replicas, the 10 nm beads were observed around the circumference of the cross-fractured erythrocytes. The number of observed beads per cell is dependent on the chance nature of the fracture and is not necessarily a measure of the actual number of beads bound to that cell. In the best cases, the beads appear regularly in a row along one side of a cross-fractured erythrocyte at intervals of 40 to 50 nm. Due to the "onion ring" effect produced by etching, it is not possible to determine exactly the distance of the beads from the erythrocyte membrane. In thin sections of the same sample, the electron dense 10 nm gold beads are also observed at the membrane surface of the erythrocyte. Freeze-etching images of CD4-bearing erythrocytes following incubation with HIV-infected H9 cells showed 100 nm "irregularities" or extrusions that have altered the distribution of membrane proteins on the erythrocyte membrane face. This suggests a fusion of the virus with the erythrocyte surface (presumably to the CD4 antigen).

Liposomes prepared with CD4 in the bilayers (as per Example 1, infra) can be examined by freeze-etching electron microscopy and are found to be both uni-and multilamellar with diameters in the range of 300 to 500 nm. After incubation of liposomes for 8 hours with HIV-infected H9 cells, virus particles are found to be attached to liposomes into which has been inserted the CD4 protein but not those without this protein. This also shows that the protein, when inserted into the membrane by the present invention, is oriented properly. Virus particles can be identified both by size (about 100 nm) and the presence of membrane proteins. Liposomes were identified by size and encapsulated dextran.

To demonstrate fusion of CD4-liposomes with infected cells and delivery of the contents of the liposome to the cell interior, the following procedure can be employed. CD4-liposomes, encapsulating ferritin (as per the general procedure of Example 1, infra), are incubated with HIV-infected H9 cells, or with normal H9 cells, for 8 hours. The cells are then washed and fixed. Liposomes without CD4, but encapsulating ferritin, are used in like fashion.

Thin-section electron microscopy showed that the liposome-encapsulated ferritin had been transferred to lipid droplets in the infected cells. Liposomes were observed inside large cytoplasmic vacuoles inside the infected cells. Instances of liposome fusion with the plasma membranes of the cells were also found. These results were not found where the liposomes did not possess the CD4 antigen.

CD4-bearing liposomes formed with phosphatidyl ethanolamine lisamine rhodamine (rhodamine being a fluorescent dye and here attached to the lipid) in the membrane and encapsulating Fl-dextran, are incubated with HIV-infected H9 cells for 8 hours, then washed and fixed. A similar procedure is followed using the same liposomes, but without the CD4 antigen being present in their bilayers.

Freeze-etching images showed virus particles attached to the liposomes bearing the CD4 antigen but not to those without it. In addition, liposomes with the CD4 antigen were shown in the process of fusing with the HIV-infected H9 cells (i.e., they exhibited apparent membrane continuities). Liposomes without CD4 antigen appeared to be resting on the cell membranes but showed no evidence of actual fusion.

Fluorescence analysis of these cells showed significant rhodamine fluorescence in experiments where the liposomes had the CD4 antigen in their bilayers, as well as the lipid-rhodamine conjugate. This fluorescence was diffuse, as well as punctuate, but in all cases was excluded from the nucleus of the cell. Diffuse fluorescence indicates that the liposome has fused with the plasma membrane of the cell. Punctuate fluorescence can be due to liposomes collecting on the cell surface but not fusing, although perhaps being in the early stages of binding and fusing. It can also be due to the sequestering of liposomal components in digestive compartments of the cell, as well as to the results of endocytosis of the liposomes. However, exclusion of the dye from the nucleus indicates that the cell is still viable.

Where the same experiment employed uninfected healthy H9 cells, only occasional fluorescence was detected from liposomes adhering at the cell surface. No significant fluorescence was detected when liposomes not bearing CD4 antigen were used, regardless of whether the H9 cells were infected or not.

Because any cells possessing the CD4 antigen will also bind to infected-cells possessing the viral glycoprotein (gp120), the use of toxin-laden cells or liposomes (having the CD4 antigen incorporated into their membranes) permits fusion of these cells or liposomes with the HIV-infected cells, with subsequent destruction of the latter before they can bind to, and fuse with, healthy T4 cells. This serves to protect the patient's immune system from further destruction by the HIV-infected cells, and hopefully at a time before it has undergone irreparable damage.

Non-limiting examples of toxins that can be advantageously used in the present invention include ricin (a protein of MW 25,000 whose toxic A chain is all that is required), abrin (a toxalbumin obtained from the seeds of certain plants), gelonin (a protein of MW 23,000 and having the advantage of being non-immunogenic) and diphtheria toxin. Most of these are commercially available. Gelonin is prepared by the method of Pihl et. al., *J. Biol. Chem.*, 255, 6947–6953 (1980). The examples of this invention are set out below are given in terms of using ricin and/or gelonin as the toxin but any suitable cytotoxic agent can be substituted for these without any major modification of the basic procedure.

Clinical Use

The modified cells making up this invention can be used to treat AIDS by selectively eliminating HIV-infected lymphocytes from the peripheral circulation. The procedure involves inserting the receptor for the AIDS virus (the CD4 antigen) into autologous red blood cell membranes. Infected cells express the gp120 fusogenic protein on their exterior surface and thus bind CD4-containing cells. In AIDS patients, lymphocytes (normally bearing the CD4 antigen) bind to HIV-infected cells (bearing the gp120 protein) and this results in spread of the infection until all cells are infected or dead, thus bringing about general failure of the immune system. Of course, an HIV-infected lymphocyte will bind to, and fuse with, any CD4 bearing cell and not just T-helper lymphocytes. As has been shown, this includes CD4-bearing red cells. Where the CD4-erythrocyte contains within it a cytotoxic agent, the fusion results in the death of both cells. In addition, since the virus itself binds to the CD4 protein, any free virus in the bloodstream would bind to CD4-bearing erythrocytes and be sequestered within them. Since erythrocytes lack genetic apparatus, the virus cannot multiply in them. Thus, there is a two fold effect: sequestering of the small amount of free virus in the blood stream and, more importantly, fusion with, and destruction of, gp120-bearing infected-lymphocytes before they can bind to healthy T-cells and spread the virus.

In addition to the injection intravenously of engineered red blood cells, the toxin can be selectively introduced into other tissues by use of liposomes. For example, infected cells present in lymph nodes can be selectively attacked by interstitial injection (e.g., between the fingers) of liposomes (bearing the CD4 antigen in their bilayers and containing gelonin, ricin or some other toxin encapsulated within the liposome) into the lymph nodes. An advantage of such method of treatment is that the liposomes generated by the methods here presented are of a size approaching that of small cells and thus would not be degraded by endocytosis following injection.

In addition, the CD4-bearing cells and liposomes making up this invention can be employed as part of an in vitro assay fro detecting the presence of gp120-bearing (i.e., infected) lymphocytes (employing the procedure of Example 5 below). Such a procedure involves the production of cells or liposomes according to this invention. The cells or liposomes making up the diagnostic reagent have CD4 antigen in their membranes, contain a cytotoxic agent in their cytoplasm, and are labeled with a radioactive substance, advantageously chromium-51. Because HIV-infected cells bear the gp120 virus protein in their membranes, such cells would fuse with the CD4-bearing, toxin containing, radiolabeled cells with subsequent release of the radiolabel into the surrounding medium.

To use this invention as a diagnostic reagent, blood is withdrawn from a patient, optionally one suspected of having AIDS, the white cells (especially the lymphocytes) are collected by standard procedures (for example, those already described in this application) and a small aliquot is mixed in vitro with an aliquot of the cells or liposomes of this invention, as described in Example 5, below, wherein liposomes are used for demonstrative purposes. After incubation at or around 37° C. for a sufficient period of time for cell fusion to occur, optimally up to 24 hours, a smaple of the cell medium is collected and the radioactivity measured. The measurement is duplicated using white cells from the blood of a normal person as a control. Detection of an elevated level of radioactivity (following calculation via a corrective formula) in the medium surrounding the cells taken from the patient relative to the control cells indicates fusion and, thereby, the presence in the patient's blood of cells containing the gp120 protein. The latter is interpreted to mean that said cells are infected with the AIDS virus and that the patient therefore has AIDS. Since antigens other than CD4 can be introduced into the membranes of the cells or liposomes of this invention, other viral diseases could be diagnosed using this procedure. Heretofore, diagnostic procedures for AIDS have commonly relied on detection of the presence of anti-HIV antibodies in the blood of patients suspected of having AIDS. However, such a finding does not necessarily indicate the occurrence of the disease but merely that the patient has been exposed to the virus or some of its antigens. The diagnostic procedure disclosed herein has the advantage of indicating the presence of infected cells in which the virus is replicating, i.e., an active infection. Applicants intend to rely on all equivalents thereof.

The cells and liposomes making up the present invention can be further utilized as a means of delivering a therapeutic amount of anti-viral drugs directly to cells such as macrophages and Kuppfer cells. The latter types of cells (part of the reticuloendothelial system) do not possess receptors for HIV. However, HIV-infected cells express foreign antigen on their surfaces and are eventually taken up and phagocytozed by macrophages and Kuppfer cells. It is believed that this route is used by the virus to infect cells of the reticuloendothelial system despite these cells' of CD4 antigen on their surfaces. To protect these cells from harboring the virus and allowing its replication, the cells and liposomes of the present invention can be used to deliver a therapeutic amount of an anti-AIDS drug directly to macrophages, Kuppfer cells and other cells of the reticuloendothelial system. This has the effect of protecting these phagocytic cells from becoming infected with the virus following their ingestion of infected cells and other virus contaminated debris.

By way of example, such anti-AIDS chemotherapeutic agents as AZT (azido-3'-deoxythymidine), ribavarin and DDC are readily encapsulated within the cells and liposomes of the present invention. This is most easily accomplished by using the encapsulation procedure described in U.S. Pat. No. 4,652,449, issued Mar. 24, 1987, the entire disclosure of which is specifically incorporated herein. Either before or after the encapsulation of the therapeutic agent, the procedures of the present invention are used to insert the appropriate antigenic protein (CD4 where AIDS is the disease to be treated) into the membrane of the erythrocytes and liposomes. The result is an erythrocyte or liposome containing therein a therapeutic quantity of an active anti-AIDS drug and which has incorporated into its membrane the CD4 antigen to serve in directing it to, and inducing fusion with a cell infected with the AIDS virus. Following fusion, this fused cellular complex is recognized as foreign (because of the virus-coded proteins in the membrane of the infected cell or cells) and phagocytozed by macrophages and other reticuloendothelial cells. As a result, the anti-AIDS drug is introduced directly into the phagocytic cells and prevents viral replication in those cells, thus closing off another avenue by which the virus can replicate itself.

The advantages of such a procedure are that the drug is not free in the blood stream and thus is not available to cause any undesirable and deleterious side effects. In addition, because the antigen in the membrane of the drug carrying cell or liposomes is specific for cells carrying the gp120 protein in their membranes (i.e., HIV-infected cells), healthy cells will not be exposed to the drug and thus any inherent toxicity of the drug will be greatly reduced. The net result is that the overall dosage of the drug can be reduced, thus reducing overall cost, while the effective therapeutic plasma concentration of the drug will also be increased (because it is not needlessly spread throughout the body). A further advantage is that, because the drug is effectively sequestered within the antigenically modified erythrocytes and liposomes, it is unable to spread throughout the tissue fluids of the body (where it is less likely that there will be any virus-infected cells).

The invention is now described with reference to the following non-limiting examples.

EXAMPLES

Example 1

Insertion of the human leukocyte antigen CD4 into the Erythrocyte Plasma Membrane a. A typical preparation of liposomes was performed as follows: the lipids to be used (which were stored prior to use at −30° C. in 2:1 (v/v) chloroform/methanol) were mixed in different proportions. The most common procedure involved mixing phosphatidyl ethanolamine (purchased from Sigma Chemical Co., St. Louis Mo., and purified according to Singleton et al., *J. Am. Oil Chem. Soc.*, Vol. 42, 53–61 (1965)), phosphatidyl choline (Sigma Chemical Co.), phosphatidyl serine (Sigma) and cholesterol (Sigma) in the molar ratio of 1:2:1:1.5, respectively, and typically a total weight of 5 mg was used. This mixture (final concentration 10 to 30 mM) was dried to a thin film under a stream of nitrogen, then in vauco for 1 hour (to remove residual traces of organic solvent). The liposomes were prepared by reverse phase evaporation (see Szoka, *Proc Nat Acad Sci U.S.A.*, Vol 75, 4194–4198 (1978)). Briefly, the lipid material was dissolved in 4.5 ml of freshly distilled ether and sonicated 15 seconds in a bath type sonicator with 1.5 ml of phosphate buffered saline (PBS). Solubilization was aided by the addition of n-octyl-D-glucopyranoside (OG) so that the detergent/lipid molar ratio was 8:1. The ether was removed under reduced pressure in a rotary evaporator and the liposome suspension was diluted to 4.5 ml with PBS or else in borate buffer, pH 7.2. Alternatively, the liposomes can be generated by the procedure described by Philippot et al., *Biochim. Biophys. Acta*, 734, 137–143 (1983), which employs adsorption on hydrophobic beads.

b. For reconstitution, a suspension of liposomes (containing 5 mg of lipid in 1 ml of borate buffer, pH 7.2) was mixed with a solution containing the proteins for incorporation. The puriffied CD4 (at a concentration of from 4 to 8 mg protein/ml in PBS containing 12 OG) was added to the lipid-detergent mixture. The ratio of lipid to protein, by weight, was maintained between 5 and 10. Dimethyl-suberimidate (purchased from Sigma) was added slowly at a temperature of 10° C. until a final suberimidate concentration of 1.5 mg/ml was attained. The mixture was then incubated for 30 minutes at a temperature of 10° C. and then dialysed against borate buffer for 2 hours at a temperature of 4° C. The resulting mixture was then chromatographed on a Sepharose 4B column in order to separate liposomes from unreacted proteins.

This procedure yields about 5,000 to 20,000 molecules of CD4 antigen per liposome. The liposomes were characterized using flow cytometry and freeze fracture. Their internal volume was found to be between 12 and 16 liters per mole of lipid and their average external diameter was found to be about 450 nm.

In addition to reconstituting with pure CD4, the procedure was also carried out using a quantity of lysozyme equal to that of CD4 as part of the protein mixture. This is then incorporated along with the CD4 and has the advantage of preventing fusion of liposomes with each other during the later fusion steps that produce modified erythrocytes.

The enzymatic activity of the lysozyme (if lysozyme is used) can be assayed by the Micrococcus leisodeikticus assay (Arvinte et al, *Proc. Natl. Acad. Sci. USA*, 83, 962–966 (1986)).

c. A volume of fresh whole blood was diluted with the same volume of phosphate buffered saline (PBS, 5 mM phosphate, 145 mM NaCl, pH 7.4, and separated from plasma by centrifugation (640 g for 30 minutes at 4° C.). Both the supernatant and the buffy coat of white cells were discarded. Polymorphonuclear leukocytes were removed by absorbent cotton filtration. The erythrocytes are then resuspended in PBS, pH 7.4, followed by 3 more washes (each with centrifugation at 2000 rpm for 30 minutes at 4° C.).

d. The hematocrit was adjusted to 70% and the erythrocytes (about 5–10 million) were then incubated with an equal volume of liposome suspension (with or without lysozyme and using sufficient liposomes to give a ratio of 1 to 10 liposomes per red cell) and 1.4 m) of sodium acetate buffer (0.02M sodium acetate/0.145M NaCl) at final pH 5.5 for 30 minutes at a temperature of 37° C. The erythrocytes were then collected by centrifugation at 1400 g for 20 min at 20° C. Immunofluorescence assay with fluorescent-labeled anti-CD4 antibodies was used to quantitatively measure the presence of CD4 antigen in the plasma membranes of a small sample of the erythrocte/liposome hybrids.

Alternatively, CD4 can be inserted without the use of liposomes. Here, 1.5 mL of sodium acetate buffer (0.02N, pH 4.7, 0.145M NaCl), 60 microliters of a solution containing 0.1 to 0.4 mg of CD4 (in 1% octylglucoside) and 30 microliters of red blood cell suspension (produced by combining 50 microliters RBC pellet with 1 mL PBS, pH 7.4) are mixed in an Eppendorf centrifuge tube (15 mL size was convenient) and incubated at 37° C. for 60 to 90 seconds. The above 3 solutions (buffer, protein and RBC) should be warmed to 37° C. prior to mixing. After incubation, 10 mL of PBS, pH 7.4, was added (to halt exposure of cells to low pH) and the cells were then concentrated by centrifugation of the reaction mixture at 3000 rpm for 4 min in the fixed angle rotor of an Eppendorf centrifuge. The supernatant was removed and the cells then resuspended in PBS, pH 7.4. Three additional washes were performed in PBS, under the same conditions.

Example 2

Measurement of Incorporated CD4 Antigen

The presence of antigenic activity of the incorporated CD4 antigen was measured using fluoresccin-isothiocyanate labeled anti-CD4 antibodies by the procedure of fluorescence-activated cell sorting (using an Epics V cell sorter from Coulter). For this determination, 2 samples were used:

Sample A: Red blood cells into which CD4 molecules had been incorporated.

Sample B: Red blood cells containing no CD4 protein.

In the following description, FITC refers to fluorescein isothiocyanate, a fluorescent label for protein chains.

The procedure used was as follows:

Both samples, A and B, were washed with PBS, pH 7.4, and concentrated by centrifugation (at 3000 rpm for 4 minutes in an Eppendorf centrifuge). Over the cell pellets, each about 10 microliters, there was layered, in each experiment, a solution of one of the following monoclonal antibodies:

1. 10 microliters of "Anti-T4-FITC" (Pel-Freez monoclonal antibody, M 102-10-OAX, Brown Deer, Wis. 53223).

2. 10 microliters "Leu-3a-Pe" (Anti-human Leu-3a Phycoerythrin conjugate from Becton Dickinson, Mountain View, Calif. 94039).

3. 10 microliters ("OKT-4A-FITC" (Ortho-mune OKT-4a Murine monoclonal antibody-FITC conjugate, Anti-human inducer/helper T Cell, from Ortho Diagnostic Systems, Inc., Raritan, N.J. 08869).

The suspension was agitated to mix the cell mass with the antibody solutions. The cells were allowed to react with the fluorescence labeled anti-CD4 antibodies for 15 minutes at 22° C.

After incubation, 1 ml of PBS, pH 7.4, was added to the 2 samples and the cells suspensions again concentrated by centrifugation (as above). The supernatants (A and B) contained the antibodies that did not bind to the cells and these were removed. The process of washing with PBS and concentrating by centrifugation was repeated twice with removal of each of the supernatants.

The cells were suspended in PBS and examined. Only the cells from sample A were fluorescent by microscopy, spectrophotometry and FACS assay, so that only they could be considered to have incorporated the CD4 antigen into their membranes.

In addition, the amount of fluoresent material (FITC) in the pooled supernatants was measured by fluorescence spectroscopy using an excitation wavelength of 470 nm and an emission wavelength detection at between 480 and 600 nm.

Protein fluorescence measurements utilized an excitation wavelength of 280 nm with the same emission range as above.

The difference in the fluoresent intensities between the pooled supernatants, A and B, was directly proportional to the amount of fluorescent label bound to the erythrocytes. Therefore, knowing the initial antibody concentration and the number of red blood cells, it was simple to calculate the mean value for the number of CD4 molecules per cell.

In the above procedure, each sample, A and B, contained about 14 million cells and the total amount of fluorescent monoclonal antibodies was about 0.0021 mg. The average molecular weight of CD4 antigen is about 58,000 daltons so that each incubation mixture contained roughly 7 trillion antibody molecules. Using these values where R=Fluorescence of Supernatant A/Fluorescence of Supernatant B and N=No. antibody molecules X (1−R)

and from the protein fluorescence spectra (excitation=280 nm) the value calculated was R=1.1. The corresponding value for FITC fluorescence was R=1.33.

Assuming that the CD4 molecules in the cell membranes were saturated by the antibodies, the number of bound antibodies equals the number of incorporated CD4 molecules (N in the above formula). Using R=1.1, the value for N was 37,000. Using R=1.33, the value was N=59,300. The value used depends on whether you measure protein fluorescence or protein-bound FITC fluorescence and the result is therefore a means of these values. Therefore, our calculations showed between 37,000 and 60,000 CD4 molecules per cell.

Example 3

Encapsulation of Ricin Toxin in Erythrocytes

A. Erythrocytes prepared in accordance with the procedure given in Example 1 were washed several times with chilled 0.15M NaCl and centrifuged to give a pellet. The cells were then resuspended in PBS at pH 7.4.

b. The suspension of erythrocytes was then washed with a solution containing up to 0.1 mM of pure ricin toxin (purified A chain from Sigma Chemical Co.) in PBS, pH 7.4. The erythrocytes were centrifuged at 1000 g for 10 minutes, the supernatant decanted and the final hematocrit adjusted to 70% with saline.

c. The erythrocyte suspension was cooled to 4° C. and allowed to flow continuously into the blood compartment of a conventional hemodialyzer having a dialysis surface of 0.41 square meters and a membrane thickness of 13.4 microns. Constant erythrocyte flow rate of 20 to 60 ml/minute was maintained with a peristaltic pump. The hemodialyzer was fed at a constant flow rate of 500 ml/minute with a low ionic strength buffer (0.01M sodium phosphate, 0.01M sodium bicarbonate, 0.002M glucose) at pH 7.4 and temperature maintained at 4° C. During this dialysis step the erythrocytes were lysec and collected at 37° C. before being resealed through the addition of a tenth volume of a hypertonic solution containing (per liter) 1M chloride salt with a K to Na ratio of 8.3 (in order to maintain a high ATP content in the resealed cells).

d. The cell suspension was then collected and maintained at 37° C. for 30 minutes to permit resealing of the cells. The erythrocytes are then washed twice with a 0.15M NaCl solution containing (per liter) 1 mM calcium chloride, 1 mM magnesium chloride, and 2 mM glucose. The erythrocytes are then suspended the native autologous plasma before infusion at a chosen hematocrit.

Example 4

Alternative Procedure for Encapsulation of Ricin or Gelonin Toxins into Erythrocytes a. Beginning with the same lipid mixture of example 1 and taking it through the evaporation of residual organic solvents, the toxic material (e.g., ricin, gelonin, etc) to be encapsulated was introduced in HEPES buffer (10 mM HEPES (pH7.4)/1 mM EGTA/150 mM NaCl) as per the procedure described by Philippot et al. Sufficient toxin was used to give a final value of about 0.01 to 0.02 micrograms per billion liposomes. The two phase system was vortexed briefly and the lipids were hydrated 30 minutes at a temperature above the highest transition temperature of the components in the mixture. Small amounts of detergent (Triton X-100) were added and the volume of the samples was adjusted to 0.625 ml with HEPES buffer. After vigorous shaking the detergent was removed.

b. Three different techniques were used to remove detergent:
  i. The sample was placed in a dialysis bag 1 cm wide and dialyzed against 1 liter of 0.01M Tris-MCl (pH 7.4)/1 mM EDTA/0.15M NaCl with 4 changes of the medium.
  ii. The volume of dialysis medium was reduced to 100 ml and Bio-Beads (type SM-2 from Bio-Rad, Richmond, Calif.) were added outside the bag in the buffered medium. The medium was not changed.
  iii. In some experiments the Bio-Beads were added directly to the liposome preparation in a test tube, and placed on a rotary mixer running at 10 RPM for at least 3 hours.

c. When necessary, the liposome suspension was passed through a Sepharose 4B column to remove the non-encapsulated material. The ricin containing liposomes are then used for the insertion of lysozyme and CD4 as in Example 1.

d. The erythrocytes are then incubated with the ricin- (or gelonin-) containing liposimes as described in Example 1. The fusion efficiency was monitored by fluoescence microscopy and by FACS analysis. For larger scale preparations the procedure can be carried out using ricin without the fluorescein label since the latter was needed only for monitoring purposes.

Example 5

In Vitro Interaction of HIV-Invected Cells with CD4-Liposomes Containing Gelonin a. A T-cell population, H9, was cloned from the HT cell line and some of the cells were persistently infected with HIV isolate. The cells are then cultured in RPMI 1640 medium (containing 10% decomplemented fetal calf serum, 0.2 mM glutamine) as described in Yoffe et al., *Proc. Nat. Acad Sci*, U.S.A., 84, 1429–1433 (1987). H9/HIV cells are morphologically indistinguishable from uninfected cells when examined by light microscopy. Thus, virus production by the H9/HIV cells was monitored by electron microscopy, as well as a standard reverse transcriptase assay.

b. Cells containing the CD4 antigen were obtained from blood donors, some of whom were negative for anti-HIV antibody and some of whom were positive (as described in Yoffe et al., supra).

c. The cells were labeled using 0.5 mCi of (Cr-51)-sodium chromate (from New England Nuclear, Boston, Mass.) for 90 minutes at 37° C. and then washed three times with phosphate-buffered saline. The labeled cells were then plated into culture dishes at a concentration of 10,000 cells per well.

d. CD4-liposomes, CD4-liposomes plus free gelonin, and CD4-liposomes encapsulating gelonin were each added to separate wells containing T-cells at a ratio of 5 liposomes per T-cell. Both non-infected H9 cells and infected HIV/H9 cells are then incubated separately with each of the liposome preparations for 18 hours at 37° C.

e. After incubation, a 100 microliter aliquot of the supernatant fluid from the cultures was collected and the radioactivity was measured by liquid acintillation. For each run the experiment was done in triplicate (i.e., 3 cultures are used for each run). The results are interpreted in terms of the percent specific chromium-51 release (SP REL) which indicates the extent of cell fusion and is defined by the formula:

$$SP\ REL = \frac{ER - SR}{MR - SR}$$

where
ER=experimental release
MR=a maximal release
SR=spontaneous release

The spontaneous release (SR) was measured by harvesting a 0.1 ml aliquot from the supernatant fluid in wells containing only labeled cells (i.e., H9 or HIV/H9).

Maximal release was measured by removing 0.1 ml of supernatant fluid from labeled cells lysed with 0.1 ml of 1% Triton X-100.

Radioactivity was measured using a well counter.

f. Following the 18 hour incubation both the H9 cells and the HIV/H9 cells were harvested, washed and stained by conventional procedures with trypan blue to determine the extent of survival.

Significant amounts of Cr-51 release were observed only in experiments where HIV-infected H9 cells were exposed to liposomes containing both CD4 antigen and gelonin and not where only CD4-liposomes were used or where the gelonin was free in the medium and not encapsulated within the CD4-liposome. Results for this experiment are shown in Table 1 hereinbelow.

TABLE 1

Cr-51 release following fusion of engineered liposomes with infected and normal H9 cells

| WELL # | Cells | Liposomes Prep. | Spec. Rel. |
| --- | --- | --- | --- |
| 1 | H9 | — | 2800 cpm |
| 2 | H9 | CD4-liposomes | 2800 cpm |
| 3 | H9 | CD4-liposomes + free gelonin | 2800 cpm |
| 4 | H9 | CD4-liposomes (containing gelonin) | 2800 cpm |
| 5 | HIV/H9 | — | 2800 cpm |
| 6 | HIV/H9 | CD4-liposomes | 2800 cpm |
| 7 | HIV/H9 | CD4-liposomes + free gelonin | 2800 cpm |
| 8 | HIV/H9 | CD4-liposomes (containing gelonin) | 5700 cpm |

Specific release given as cpm per 10,000 cells following an 18 hour incubation at 37° C. as per Example 5.
*# free gelonin concentration was 0.02 mg per $10^{11}$ liposomes.

Example 6

Clinical Treatment of Anti-HIV Positive Patients With Engineered Erythrocytes

A human patient who has tested positive for anti-HIV antibodies is treated with engineered red cells containing ricin, abrin, gelonin or diphtheria toxin as follows. The patient is injected intravenously (e.g., in the arm) with up to 20 ml of a saline suspension of packed engineered red cells (wherein virtually all of the cells contain the CD4 antigen and cytotoxin). The patient's condition is monitored by measuring the level of anti-HIV antibodies in the circulation as well as the general progress of his condition. The initial injection can be followed up by additional injections as the physician deems warranted.

Example 7

Clinical Treatment of Patients With ARC Using Liposomes and Engineered Erythrocytes Human patients believed to have ARC (AIDS Related Complex) are treated for the condition in much the same way as in Example 6. However, here the patients are injected with a combination of engineered red cells and liposomes (both containing CD4 in their membranes and cytotoxin. In this disease condition the main target is the lymph nodes so that advantageously the patient is injected interstitially (e.g., between the fingers) with a mixture of about 100 billion liposomes and an optimally active amount of modified erythrocytes. The patient's condition is monitored as in Example 6 and additional treatments given as needed.

Example 8

Clinical Treatment of Anti-HIV Positive Patients With Engineered Erythrocytes Containing AZT A human patient who has tested positive for anti-HIV antibodies or by the diagnostic procedure disclosed in this application is treated with the antigenically modified red cells or liposomes of the present invention containing azido-3'-deoxythymidine (AZT) as follows. The patient is injected intravenously (e.g., in the arm) with up to 20 ml of a saline suspension of packed red cells or liposomes (wherein virtually all of the cells or liposomes contain the CD4 antigen and a cytoplasmically sequestered therapeutic amount of AZT). Such treatment is adjusted by the clinician so that the total dosage of the drug is kept within safe limits, optimally between 100 to 300 mg per 4 to 6 hour period. The patient's condition is then monitored by measuring the presence of anti-HIV antibodies in the circulation (or via the diagnostic procedure set forth in the application) as well as the general progress of his condition. The initial injection can then be followed up by additional injections every 4 to 6 hours as the attending physician deems warranted.

It is understood that the specification and claims are illustrative but not limitative of the present invention and that other embodiments within the spirit and scope of the invention will suggest themselves to those skilled in the art.

What is claimed is:

1. A mammalian-derived red blood cell containing a recombinant human CD4 protein inserted into its cellular membrane which induces the mammalian-derived red blood cell to selectively bind to and fuse with a target, wherein the mammalian-derived red blood cell's life span is about a normal red blood cell's life span and wherein the recombinant human CD4 protein is non-immunogenic.

2. The mammalian derived red blood cell according to claim 1, further comprising one or more cytotoxic agents incorporated therein.

3. The mammalian derived red blood cell according to claim 2, wherein the cytotoxic agent is a protein.

4. The mammalian derived red blood cell according to claim 2, wherein the cytotoxic agent is selected from the group consisting of ricin, abrin, gelonin, and diphtheria toxin and toxicologically active fragments thereof.

\* \* \* \* \*